United States Patent
Kim et al.

(10) Patent No.: US 6,355,811 B1
(45) Date of Patent: Mar. 12, 2002

(54) POLYOXYPROPYLENEPOLYETHYLENE VITAMIN E AND PREPARATION THEREOF

(76) Inventors: Youngdae Kim; Keunja Park, both of 3-1407, Sunkyung APT, #506, Taechi-dong, Kangnam-gu; Jungsoo Kim; Jisoo Kim, both of 3-1407, Sunkyung APT, #506, Taechi-dong, Kangnam-ku, all of Seoul 135-280 (KR)

( * ) Notice: Subject to any disclaimer, the term of this patent is extended or adjusted under 35 U.S.C. 154(b) by 0 days.

(21) Appl. No.: 09/701,719

(22) PCT Filed: Jun. 1, 1999

(86) PCT No.: PCT/KR99/00270

§ 371 Date: Mar. 2, 2001

§ 102(e) Date: Mar. 2, 2001

(87) PCT Pub. No.: WO99/62896

PCT Pub. Date: Dec. 9, 1999

(30) Foreign Application Priority Data

Jun. 3, 1998 (KR) .............................. 98-20705

(51) Int. Cl.⁷ .............................. C07D 311/72
(52) U.S. Cl. ................ 549/408; 549/412; 514/458; 514/844; 424/59
(58) Field of Search ................. 514/458, 844; 549/408, 412; 424/59

(56) References Cited

U.S. PATENT DOCUMENTS 5,235,073 A * 8/1993 Kim et al. ............... 549/408
5,352,696 A * 10/1994 Kim ........................ 514/458
5,441,725 A * 8/1995 Kim et al. ............... 424/59

* cited by examiner

*Primary Examiner*—James H. Reamer
(74) *Attorney, Agent, or Firm*—Mathews, Collins Shepherd & Gould, P.A.

(57) ABSTRACT

Disclosed is polyoxypropylenepolyoxyethylene vitamin E, represented by formula (I). It is prepared by subjecting vitamin E to polyethoxylation and then, to polypropoxylation to a proper extent. The vitamin E is of superior anti-oxidation activity with water solubility. The bent chain of the polyoxypropylenepolyoxyethylene vitamin E increases the cross-sectional area of the whole molecule, making it difficult for the molecule to penetrate into the skin. It is very safe to apply to the skin. The polyoxypropylene-polyoxyethylene vitamin E has superb surface activity by forming close bilayer vesicle structures, like phospholipids or dialkyl surfactants, so it can be advantageously used in the cosmetic industry, the food industry and the medical industry. In said formula, $R_1$ is —$(OCH_2CH_2)_m$— wherein m is an integer of 0 to 150; $R_2$ is (a) wherein n is an integer of 1 to 200; A is (b) or (c); B is —$CH_3$ at the 5-, 7- or 8-position of vitamin E; and p is an integer of 1 or 3.

12 Claims, 7 Drawing Sheets

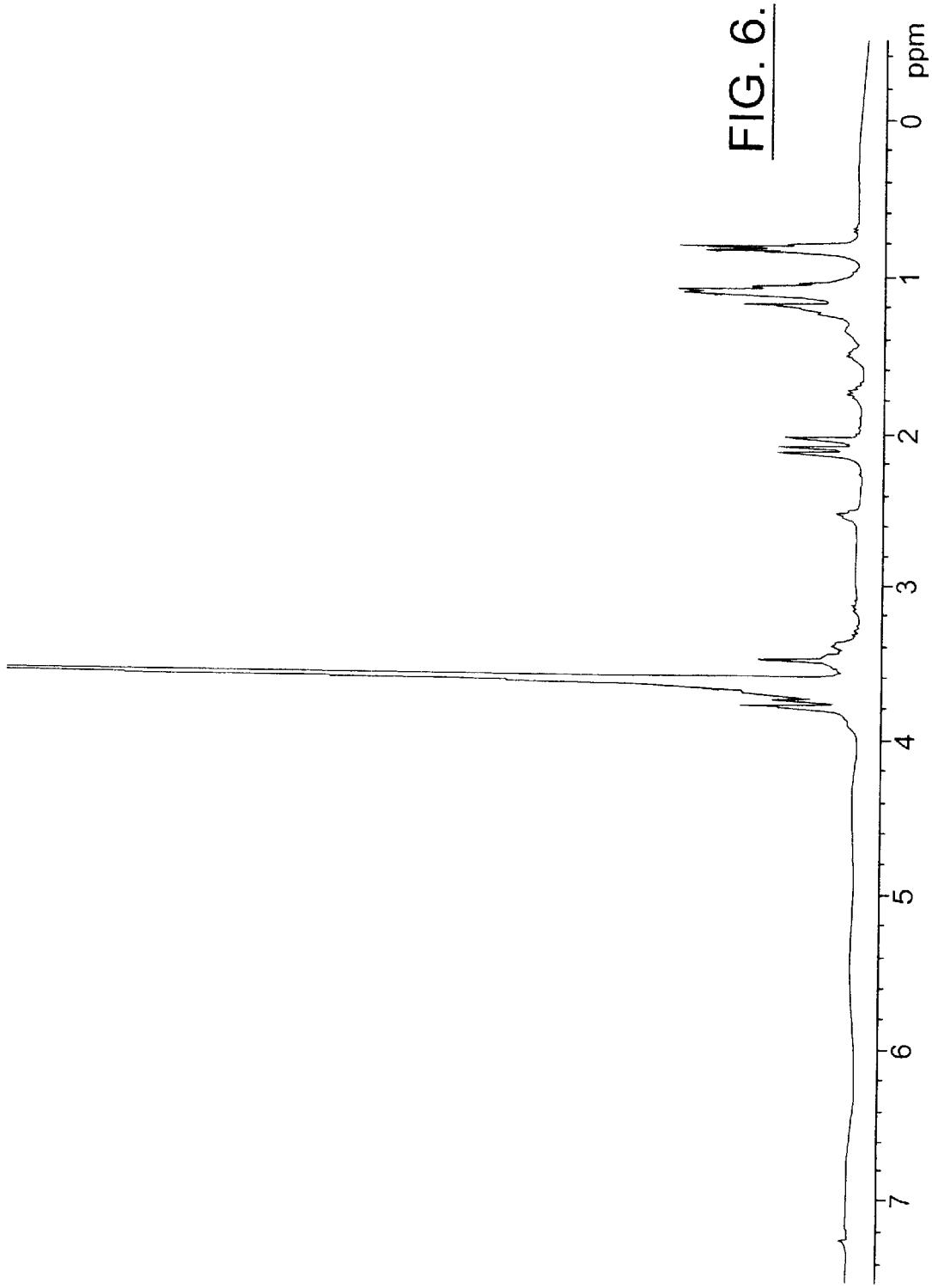

POLYOXYPROPYLENEPOLYETHYLENE VITAMIN E AND PREPARATION THEREOF

TECHNICAL FIELD

The present invention relates to novel polyoxypropylene-polyoxyethylene vitamin E and a method for preparing the same. More particularly, the present invention relates to amphipatic polyoxypropylenepolyoxyethylene vitamin E which is of high surface activity with excellent safety for the skin. Also, the present invention is concerned with the uses of such novel polyoxypropylenepolyoxyethylene vitamin E.

BACKGROUND ART

Generally, surfactants are adsorbed to the interfaces or surfaces of aqueous solutions to significantly reduce the interfacial tension or surface tension of the solutions. Depending on the concentration in a solution, surfactants form various types of micelles, which are an assembly of molecules or ions, of which advantage can be taken for various purposes.

The lipids which are of surface activity in vivo (bio-surfactants) play a role in regulating the physiological activities of organs and tissues. Bio-surfactants, which can be industrially manufactured, have useful purposes in a wide range of industries, including medicines, foods, cosmetics, etc., with classification into dispersants, emulsifiers, solubilizers, foaming agents, anti-foaming agents, polishing agents, slipping agents, surface-treating agents, wetting agents, etc. In addition to such function and purpose, ionic property is also a classification standard for surfactants, leading to ionic and non-ionic surfactants, and the latter may be further classified into hydrophilic and lipophilic surfactants. While the water solubility of ionic surfactants is attributed to the presence of ions in hydrophilic groups, non-ionic surfactants exhibit water solubility by virtue of their hydrogen bond with water.

It is known that the abundance of ionic materials in animal bodies forces non-ionic materials to be of higher bio-adaptability than ionic materials. In fact, non-ionic surfactants are generally used for the products which are applied to living bodies.

Hydrophilic non-ionic surfactants do not contain hydrophilic atomic groups which are ionized, and representative are those which have a hydroxy (—OH) group. Also, hydrophilic non-ionic surfactants may contain intramolecular ester bonds (—CO.O—), acid amide bonds (—CO.NH—) and/or ether bonds (—O—) although they all are weaker in hydrophilicity than a hydroxy group.

Of hydrophilic non-ionic surfactants, the most widely used and important are polyethylene glycol condensates which are exemplified by fatty acid polyethylene glycol condensates (Niosol, Myrj), fatty acid amide polyethylene glycol condensates, aliphatic alcohol polyethylene glycol condensates (Leonil, Peregal C), aliphatic amine polyethylene glycol condensates, aliphatic mercaptane polyethylene glycol condensates (Nyon 218), alkylphenyl polyethylene glycol condensates (Igepal), and polypropylene glycol polyethylene glycol condensates (Pluronics). Besides, various non-ionic surfactants which have complicated structures have recently been developed and utilized in various purposes, demonstrating their importance.

Generally, as aforementioned, ionic and non-ionic surfactants both are known to form micelles, which are an assembly of ions or molecules. As to why they form micelles, there are various differences between ionic surfactants and non-ionic surfactants. The formation of micelles is one of the most important properties which surfactants have, and is greatly affected by the structures of surfactants. Taking advantage of these properties, a great number of surfactants have been developed with their own purposes. The mechanism in which non-ionic surfactants form micelles in aqueous solutions can be revealed by the research on the surface tension, light diffusion and interaction with pigment of the micelles and other research. The cause of non-ionic surfactants forming micelles is the property in which the alkyl chains of the surfactant molecules are extricated from an aqueous phase by the adhesion force of water when they reach a critical concentration. In other words, the structure of a micelle is inherent in the structure of the non-ionic surfactant molecules, specifically in their amphipatic character. These properties and structural characteristics of non-ionic surfactants are primarily determined by the hydrophobic alkyl structure of the surfactant molecules. In fact, hydrophobic interactions are the major driving force for the formation of micelles or lipid bilayers.

The intensive and thorough research on new surfactants for skin care, repeated by the present inventors, led to the finding that, because vitamin E was well inserted into the ordered, dense lipid bilayers of cell membranes to protect the oxidation of the cell membranes, vitamin E played an efficient role as a hydrophobic group if it was applied to surfactants. As a result of the research, polyoxyethylene vitamin E was invented by subjecting vitamin E to addition reaction with ethylene oxide and patented with its high surface activity, skin soothing and moisturizing action, and cell protection from harmful active oxygen (Korean Pat. No. 083024, U.S. Pat. No. 5,235,073 and Japanese Pat. Appl'n No. Hei 4-10362). By virtue of its structural characteristics, the polyoxyethylene vitamin E is well absorbed into the interface, showing excellent surface activity. However, there is demanded an improvement in the safety for the skin. Because the hydrophobic, flat, hard chromane ring moiety piles up one by one neatly while the terminal phytyl group has a relatively small sectional area as well as fluidity, the polyoxyethylene vitamin E is too well inserted into the lipid bilayers of cell membranes, causing a problem in safety. This safety problem may be overcome by controlling the length of the ethylene oxide chain of the surfactant, that is, by extending the ethylene oxide chain. In this case, however, the polyoxyethylene vitamin E is too hydrophilic to exhibit a desirable surfactant function.

DISCLOSURE OF THE INVENTION

Typically, a surfactant consists of a hydrophobic atomic group and a hydrophilic atomic group with a balanced chemical linkage therebetween. Through intensive study, the present inventor recognized that most surfactants are structured to have hydrophobic atomic groups in one end and hydrophilic atomic groups in the other hand, but all are not. For instance, the non-ionic surfactant sold under the brand name "Pluronics" has polypropylene oxide as a hydrophobic atomic group, to both sides of which ethylene oxide is repetitively added (T. H. Vaughan, J. Am. Oil Chemists' Soc. 2p, 240 (1950)), as represented by the following formula:

$$HO(C_2H_4O)_a(C_3H_6O)_b(C_2H_4O)_cH$$

wherein a, b and c each is an integer of 20 to 80. Account is needed to be taken of special examples similar to this (Synthesis of Surfactants and Application thereof. P4. 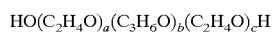 (1956 Tokyo, Japan). Hydrophilicity prevails over hydrophobicity in ethylene oxide while propylene oxide is a little more hydrophobic than hydrophilic, so their polymers, polyethylene oxide and polypropylene oxide play a role as a hydrophilic atomic group and a hydrophilic atomic group, respectively, within a certain polymerization degree (Daves, J. T., Proc. 2nd Int. Congr. Surface Activity, London 1, 426 (1953)).

As a consequence of the active research which the present inventors have made on the constituents for cell membranes with the aim of developing surfactants which are greatly improved in the safety for the skin, it was perceived that phospholipids have diacyl as a hydrophobic group and exist at a significant quantity in all living microorganisms in addition to being important constituents for all cell membranes. Synthetic or natural phospholipids are commercially used to form liposomes or vesicles. Another important point which the inventors found out is that lysophospholipids, each of which contains an acyl group, are commercially used as emulsifiers by virtue of their superior surface activity to phospholipids themselves (J. L. Harwood and N. L. Russel, Lipids in Plants an Microbes, George Allen and Unwin, London, 1984). The formation of closed, bilayer liposomes or vesicles can be easily achieved by phospholipids, but difficultly by lysophospholipids.

Fatty acids, which are components of phospholipids, are safe materials and widely used in cosmetics, skin ointments, etc. However, fatty acid have strong toxic influence on cell membranes, so they are permitted to be used in a very low concentration range; elsewise, they may break cells occasionally. In phospholipids, fatty acids are linked via ester bonds whereas trace extracellular fatty acids are in a free state. Thus, fatty acids must be esterified at any rate if they exist in intracellular regions including the envelopes (Biosurfactants Surfactant Science Series p27, Vol. 48, 1993, New York, Marcel Dekker Inc.).

From the above fact, it is recognized that surfactants which are of diacyl phospholipid structure are inferior in general surface activity such as emulsification, but superior in the ability to form liposomes or cell membrane-like vesicles as well as especially in bio-safety to lysophospholipids which are of acyl type.

With the background of the invention in mind, the present inventors have conducted further research in improving the safety of the polyoxyethylene vitamin E while maintaining its high surface activity and finally found that, if a hydrophobic moiety is added to the end of the hydrophilic moiety of the polyoxyethylene vitamin E, the resulting compound has a controlled ratio of hydrophilic group to hydrophobic group and a different orientation characteristic. In this regard, the hydrophilic polyoxyethylene chain exists between two hydrophobic moieties, so the extended alkyl chain is converted from an almost linear state to a bent state, giving rise to an increase in the sectional area of the surfactant molecule. Consequently, the vitamin E prepared is a non-ionic amphipatic material which is of excellent surface activity with great improvement in safety for the skin. This material can be prepared by subjecting vitamin E to addition with a hydrophilic polyethylene oxide chain and a hydrophobic polypropylene oxide chain, in sequence, to such an extent that the ratio of the hydrophilic group to the hydrophobic group is suitable to form vesicles.

Therefore, it is an object of the present invention to provide a novel modified vitamin E which exhibits high surface activity with reliable safety for the skin.

It is another object of the present invention to provide a novel modified vitamin E which is useful in cosmetics, foods, medicines.

It is a further object of the present invention to provide a method for preparing such a novel modified vitamin E.

It is still a further object of the present invention to provide uses of such a novel modified vitamin E.

In accordance with an aspect of the present invention, there is provided novel polyoxypropylenepolyoxyethylene vitamin E, represented by the following general formula I:

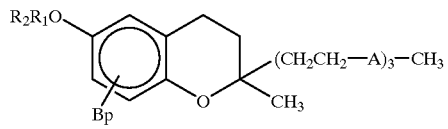

[I]

wherein, $R_1$ is —(OCH$_2$CH$_2$)$_m$— wherein m is an integer of 0 to 150;

$R_2$ is

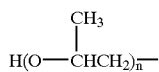

wherein n is an integer of 1 to 200;

A is

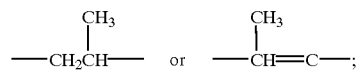

B is —CH$_3$ at the 5-, 7- or 8-position of vitamin E; and p is an integer of 1 or 3.

In accordance with another aspect of the present invention, there is provided a method for preparing the novel Polyoxypropylenepolyoxyethylene vitamin E, in which the vitamin E represented by the following general formula II, is subjected to addition reaction with ethylene oxide, represented by the following formula III, in the presence of a catalyst and then, with propylene oxide, represented by the following formula IV, in the presence of a catalyst:

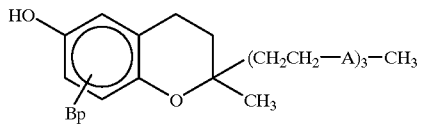

[II]

[III]

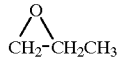

[IV]

In accordance with a further aspect of the present invention, there is provided a skin care agent containing the novel polyoxypropylenepolyoxyethylene vitamin E.

In the present invention, the polyoxypropylenepolyoxyethylene vitamin E can be prepared from natural or synthetic vitamin E. In this regard, the vitamin E is subjected to polyethoxylation and then to polypropoxylation in the presence of a catalyst. It may be a Lewis acid catalyst or an alkaline catalyst. The polyoxypropylene polyoxyethylene vitamin E prepared is tested whether it functions well as a surfactant, an anti-oxidant and a skin care agent without harmful effects on the body. In this regard, it is evaluated for anti-oxidation activity by measuring its peroxide value, for foaming ability and foam stability by dynamic foam testing, for surface tension by the du Nuoy method, and for surface activity by the formation of vesicles. As for the safety in the human body, it is confirmed through eye irritation tests and patch tests.

BRIEF DESCRIPTION OF THE DRAWINGS

The above and other objects, features and other advantages of the present invention will be more clearly understood from the following detailed description taken in conjunction with the accompanying drawings, in which:

FIG. 6 is an $^1$H-NMR spectrum of the polyoxypropylenepolyoxyethylene vitamin E (5) prepared in Example V;

BEST MODES FOR CARRYING OUT THE INVENTION

Figure 1:
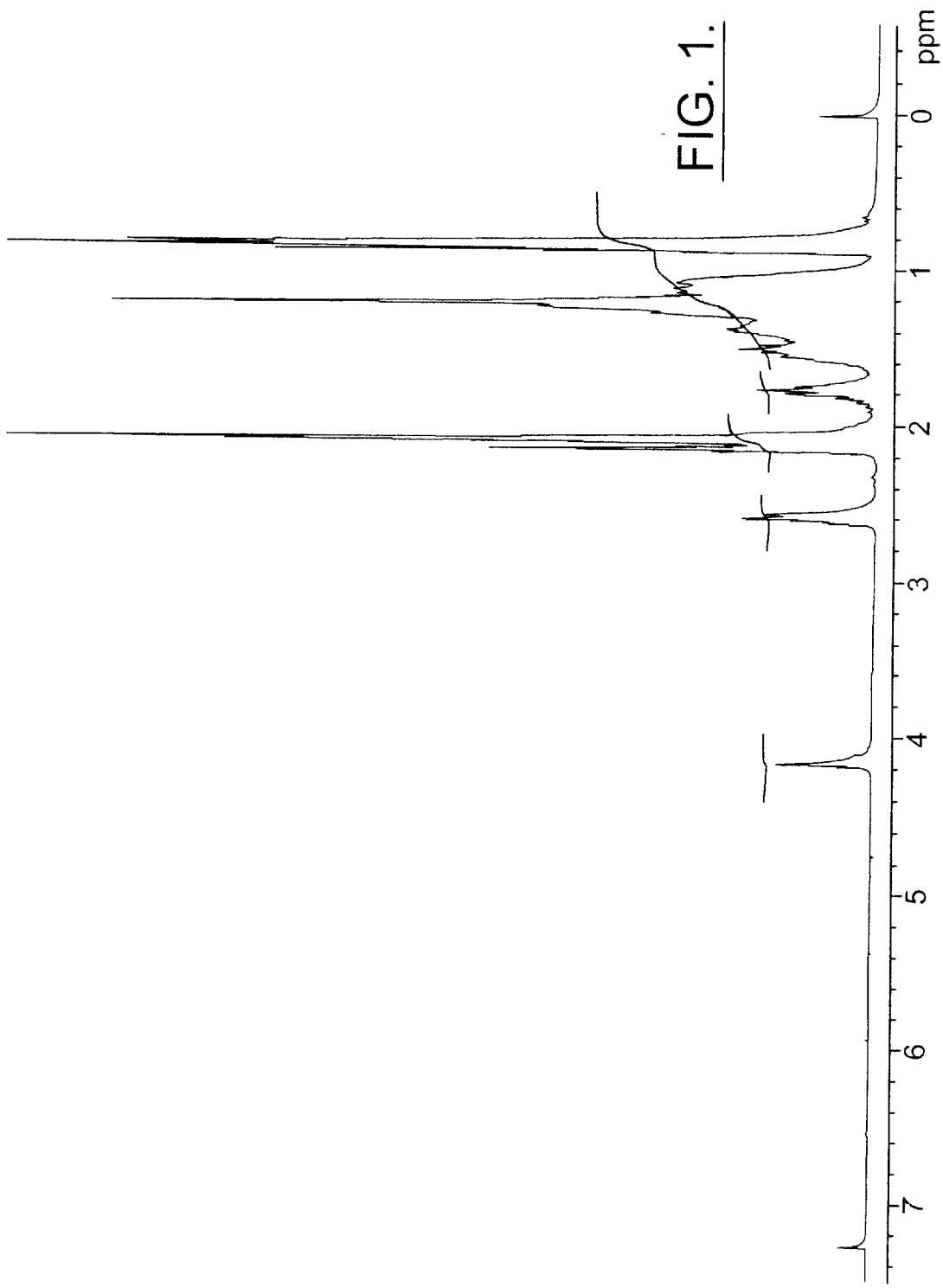
FIG. 1 is an $^1$H-NMR spectrum of synthetic vitamin E (dl α-tocopherol)

The present invention pertains to novel polyoxypropylenepolyoxyethylene vitamin E. This modified vitamin E is prepared by the sequential addition reaction of vitamin E with ethylene oxide and propylene oxide in the presence of an alkaline or Lewis acidic catalyst. When preparing the polyoxypropylenepolyoxyethylene vitamin E, account must be taken of vitamin E's being a secondary alcohol with anti-oxidation. Another account is that the reactive hydroxy group of vitamin is slowly reacted in an early reaction stage owing to the steric hindrance of neighboring $CH_3$ groups. Accordingly, pertinent selection is required for the quantity of the alkaline or acidic catalyst and the reaction temperature and pressure to be used.

As the starting material, vitamin E may be a synthetic one, such as dl α-tocopherol, or a natural one, such as that extracted from plant seeds.

Useful examples of the alkaline catalysts include $CH_3ONa$, NaOH and KOH while the Lewis acid catalyst may be selected from $BF_3$, $SnCl_4$ and $SbCl_5$. Based on the weight of the starting material or the polyoxyethylene vitamin E, the catalysts each are used at an amount of 0.02 to 0.8% by weight, but the amount may be changed depending on reaction conditions.

The addition reaction is generally carried out at a temperature of 120 to 180° C. and preferably 145 to 160° C. under a pressure of 1.0 to 8.0 kg /cm$^3$ and preferably 3.5 to 5.5 kg/cm$^2$.

A better understanding of the present invention may be obtained in the light of the following examples which are set forth to illustrate, but are not to be construed to limit the present invention.

EXAMPLE I

Preparation of Polyoxypropylenenpolyoxyethylene Vitamin E (1)

In a 1L double stainless steel autoclave were introduced 112 g (0.26 mol) of synthetic vitamin E (dl α-tocopherol) and then, 0.15 g of highly pure methoxy sodium ($CH_3ONa$). The moisture inside the reactor was removed by heating to 70° C. under vacuum of about 720 mmHg for about 20 min.

Thereafter, 132 g (3.0 mol) of ethylene oxide was added to the reactor under pressure and allowed to react at 150–160° C. for about 6 hours with stirring, so as to give 244 g of a liquid phase of polyoxyethylene vitamin E, which was somewhat dispersed in water. It was subjected to addition reaction with 35 g (0.6 mol) of propylene oxide for 8 hours at 145–155° C. in the presence of 0.1 g of methoxy sodium to give a yellow liquid phase.

After completion of the reaction, the reactor was purged three times with gaseous nitrogen to remove unreacted ethylene oxide, propylene oxide and 1,4-dioxane, a by-product. The reaction mixture was cooled to about 30° C., followed by adding a trace amount of citric acid to neutralize the alkaline catalyst. It was purified by column chromatography on Sephadex LH-50 eluting with a chloroform-methanol (1:1, v/v) to afford 265.5 g of polyoxypropylenepolyoxyethylene vitamin E(1) in a liquid phase.

(1) Appearance: a pale yellow liquid at room temperature (2) Elemental Analysis: as a relative molecular weight of $C_{55}H_{102}O_{14}$
Calculated (%): C 66.94; H 10.34; N: 0.00
Found (%): C 67.16; H 10.82; N: 0.04

(3) Yield: 95.0%

Figure 2:
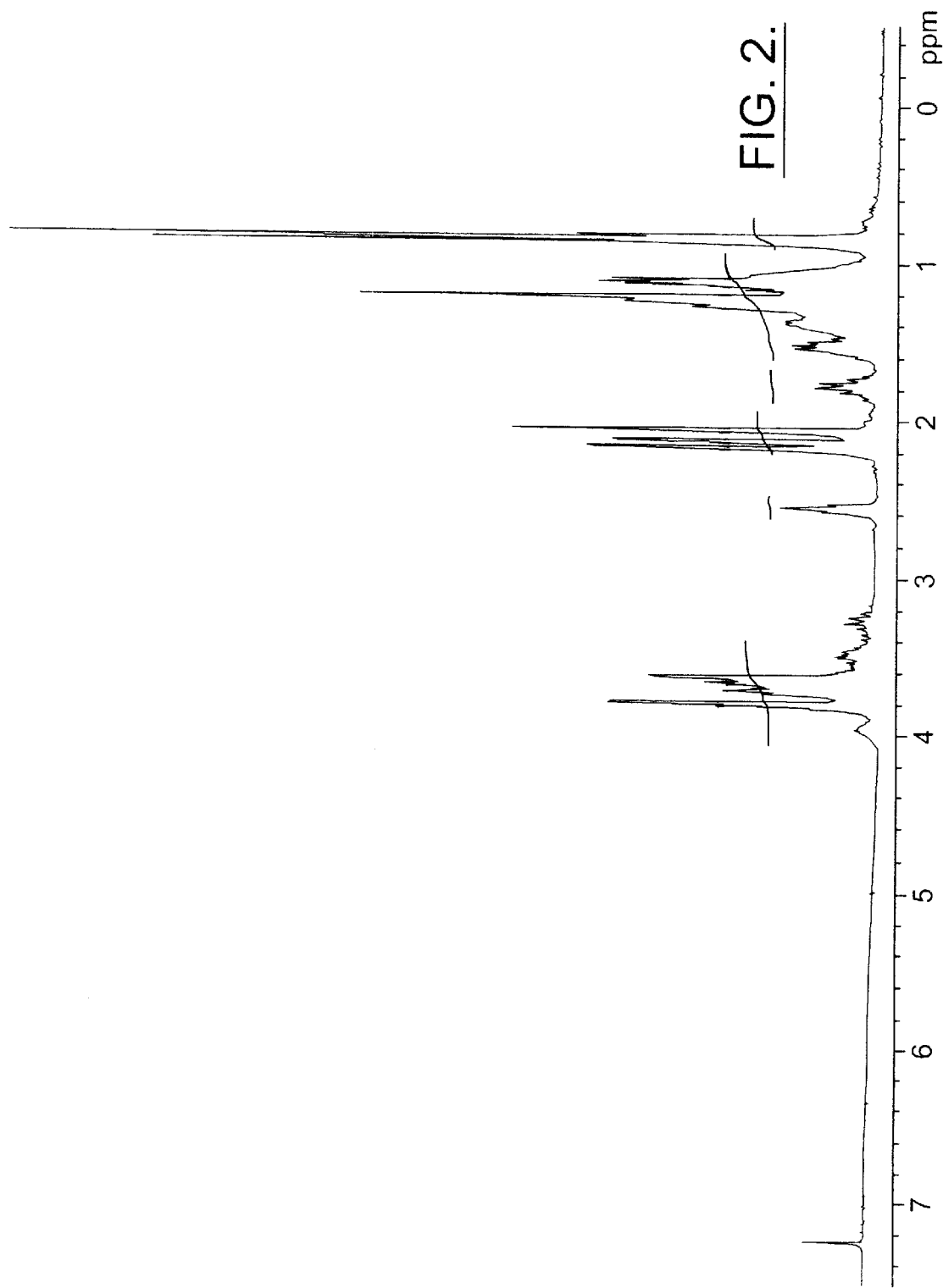
FIG. 2 is an $^1$H-NMR spectrum of the polyoxypropylenepolyoxyethylene vitamin E (1) prepared in Example I.

(4) Moles of Added Ethylene oxide: 10 moles on average (5) Moles of Added Propylene oxide: 2 moles on average (6) NMR spectrum $^1$H-NMR spectra for the synthetic vitamin E and the polyoxypropylenepolyoxyethylene vitamin E(1) are shown in FIGS. 1 and 2, respectively. As seen, the NMR spectrum of FIG. 1 has a peak for —$CH_2CH_2$— or —$CH_3$ read at 1.17–1.3 δ, three peaks for the —$CH_3$ of the phenyl group at 4.1 δ, and a peak for the —OH group of the trimethyl phenol at 4.1 δ. In FIG. 2, the peak at 4.1 δ disappears while peaks for the H of polyethylene oxide —($CH_2CH_2O$)$_m$— and for the H of the

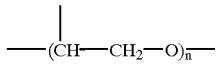

of polypropylene oxide —($CH(CH_3)$—$CH_2$—O)$_n$H appear at 3.5–3.8 δ. Also, an H peak of the end —OH of the propylene oxide appears at 3.97 δ and a peak for the —$CH_3$ of polypropylene oxide —($CH(CH_3)$—$CH_2$—O)$_n$— is additively detected at 1.3 δ.

EXAMPLE II

Preparation of Polyoxypropylenenpolyoxyethylene Vitamin E (2)

In a 1L double stainless steel autoclave were introduced 220 g (0.51 mol) of synthetic vitamin E (dl α-tocopherol) and then, 0.2 g of highly pure methoxy sodium ($CH_3ONa$). The moisture inside the reactor was removed by heating to 75° C. under vacuum of about 750 mmHg for about 20 min.

Thereafter, 130 g (3.0 mol) of ethylene oxide was added to the reactor under pressure and allowed to react at 145–155° C. for about 6 hours with stirring, so as to give 348 g of a liquid phase of polyoxyethylene vitamin E, which was somewhat dispersed in water. It was subjected to addition reaction with 70 g (0.6 mol) of propylene oxide for 8 hours at 145–155 C. in the presence of 0.1 g of methoxy sodium to give a yellow liquid phase.

After completion of the reaction, the reactor was purged twice with gaseous nitrogen to remove unreacted ethylene oxide, propylene oxide and 1,4-dioxane, a by-product. The reaction mixture was cooled to about 30° C., followed by adding a trace amount of citric acid to neutralize the alkaline catalyst. It was purified by column chromatography on Sephadex LH-50 eluting with a chloroform-methanol (1:1, v/v) to afford 405.4 g of polyoxypropylenepolyoxyethylene vitamin E(2) in a liquid phase.

Figure 3:
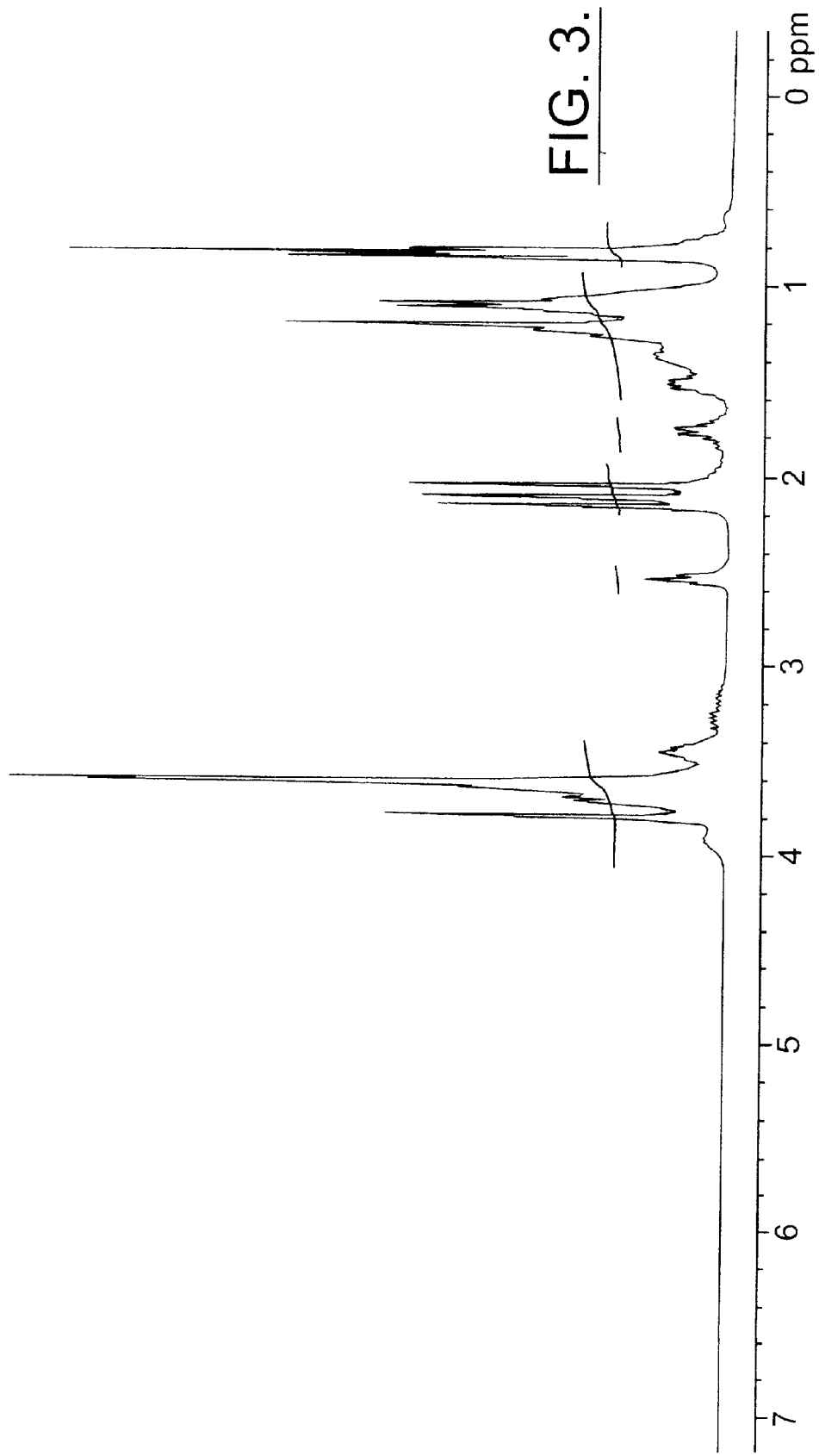
FIG. 3 is an $^1$H-NMR spectrum of the polyoxypropylenepolyoxyethylene vitamin E (2) prepared in Example II.

(1) Appearance: a pale yellow liquid at room temperature
(2) Elemental Analysis: as a relative molecular weight of $C_{45}H_{82}O_9$
   Calculated (%): C 70.5; H 10.7; N: 0.00
   Found (%): C 71.3; H 11.4; N: 0.03
(3) Yield: 96.5%
(4) Moles of Added Ethylene oxide: 5 moles on average
(5) Moles of Added Propylene oxide: 2 moles on average
(6) NMR spectrum An $^1$H-NMR spectrum for the polyoxypropylenepolyoxyethylene vitamin E(2) is shown in FIG. 3. In this NMR spectrum, when being compared with the NMR spectrum of FIG. 1, the peak for —OH at 4.1 δ disappears while peaks for the H of polyethylene oxide —$(CH_2CH_2O)_m$— and for the H of the

of polypropylene oxide —$(CH(CH_3)—CH_2—O)_nH$ appear at 3.5–3.8 δ. Also, an H peak of the end —OH of the propylene oxide appears at 3.97 δ and a peak for the —$CH_3$ of polypropylene oxide —$(CH(CH_3)—CH_2—O)_n$— is additively detected at 1.3 δ.

The spectrum of FIG. 3 is similar in pattern to, but shorter than that of FIG. 2 because the moles of the polyoxyethylene and polyoxypropylene used in this Example were fewer than those of the polyoxyethylene and polyoxypropylene used in Example I.

EXAMPLE III

Preparation of Polyoxypropylenenpolyoxyethylene Vitamin E (3)

In a 2L double stainless steel autoclave were introduced 125 g (0.29 mol) of synthetic vitamin E (dl α-tocopherol) and then, 0.2 g of highly pure KOH (99.9%). The moisture inside the reactor was removed by heating to 77° C. under vacuum of about 740 mmHg for about 30 min.

Thereafter, 300 g (6.8 mol) of ethylene oxide was added to the reactor under pressure and allowed to react at 160–165 C. for about 6 hours with stirring, so as to give a liquid phase of polyoxyethylene vitamin E, which was well dispersed in water. It was subjected to addition reaction with 95 g (1.69 mol) of propylene oxide for 8 hours at 155–160° C. in the presence of 0.15 g of KOH (99.9%) to give a yellow liquid phase.

After completion of the reaction, the reactor was purged three times with gaseous nitrogen to remove unreacted ethylene oxide, propylene oxide and 1,4-dioxane, a by-product. The reaction mixture was cooled to about 40° C., followed by adding a trace amount of citric acid to neutralize the alkaline catalyst. After unreacted vitamin E was removed with toluene, the reaction was purified by column chromatography on Sephadex LH-50 eluting with a chloroform-methanol (1:1, v/v) to afford 505.7 g of polyoxypropylenepolyoxyethylene vitamin E(3) in a liquid phase.

Figure 4:
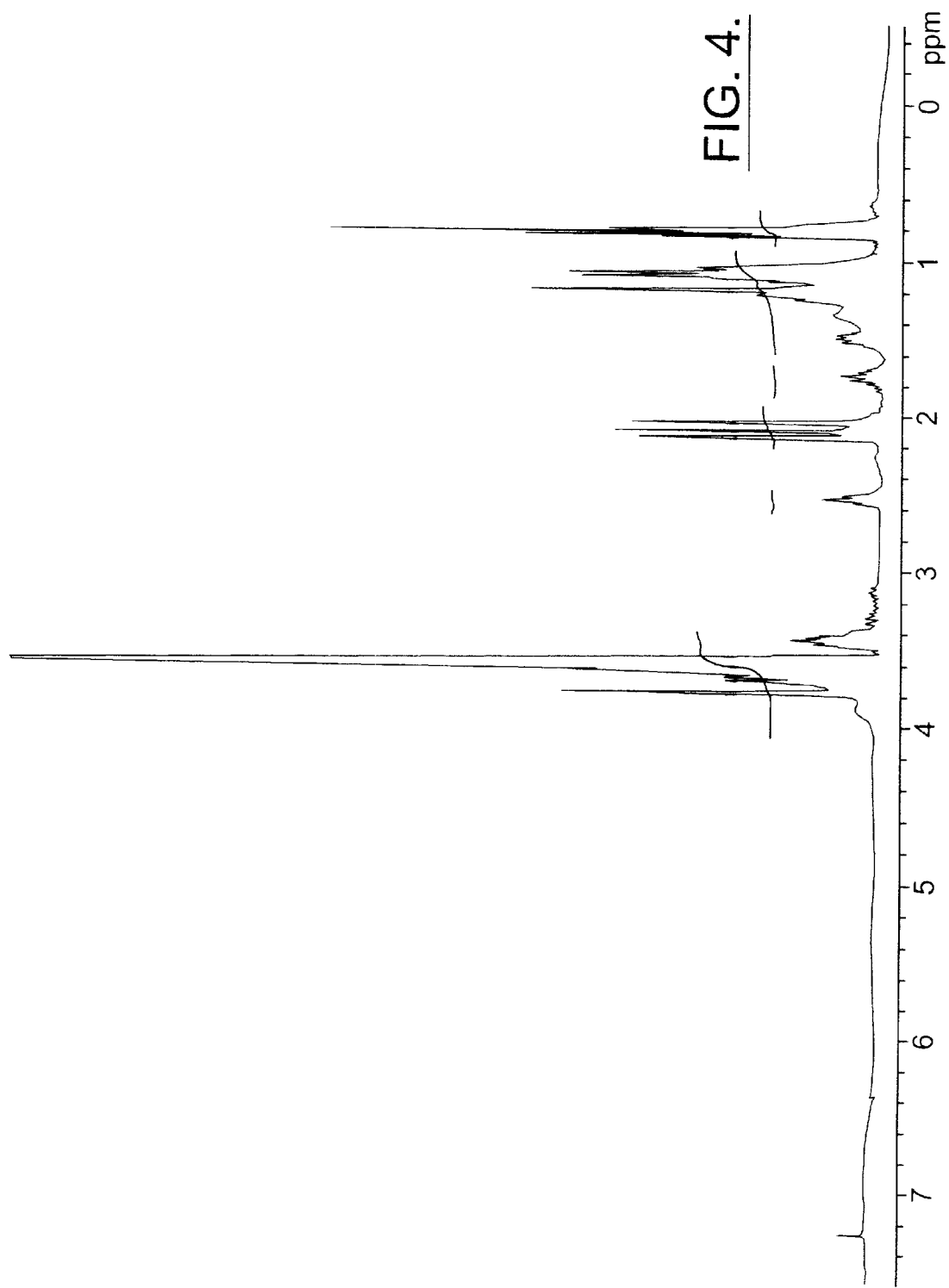
FIG. 4 is an $^1$H-NMR spectrum of the polyoxypropylenepolyoxyethylene vitamin E (3) prepared in Example III.

(1) Appearance: a pale yellow semi-solid phase at room temperature
(2) Elemental Analysis: as a relative molecular weight of $C_{85}H_{160}O_{27}$
   Calculated (%): C 63.28; H 9.93; N: 0.00
   Found (%): C 64.21; H 10.7; N: 0.03
(3) Yield: 97.3%
(4) Moles of Added Ethylene oxide: 20 moles on average
(5) Moles of Added Propylene oxide: 5 moles on average
(6) NMR spectrum An $^1$H-NMR spectrum for the polyoxypropylenepolyoxyethylene vitamin E(3) is shown in FIG. 4. In this NMR spectrum, when being compared with the NMR spectrum of FIG. 1, the peak for —OH at 4.1 δ disappears while peaks for the H of polyethylene oxide —$(CH_2CH_2O)_m$— and for the H of the

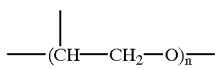

of polypropylene oxide —$(CH(CH_3)—CH_2—O)_nH$ appear at 3.5–3.8 δ. Also, an H peak of the end —OH of the propylene oxide appears at 3.97 δ and a peak for the —$CH_3$ of polypropylene oxide —$(CH(CH_3)—CH_2—O)_n$— is additively detected at 1.3 δ.

The spectrum of FIG. 4 is similar in pattern to, but taller than that of FIG. 2 because the moles of the polyoxyethylene and polyoxypropylene used in this Example were more than those of the polyoxyethylene and polyoxypropylene used in Example I.

EXAMPLE IV

Preparation of Polyoxypropylenenpolyoxyethylene Vitamin E (4)

in a 2L double stainless steel autoclave were introduced 234 g (0.56 mol) of natural vitamin E (α, β, γ, δ-tocopherol mixture), extracted from plant seeds, and then, 0.15 g of highly pure methoxy sodium ($CH_3ONa$). The moisture inside the reactor was removed by heating to 75° C. under vacuum of about 750 mmiHg for about 25 min.

Thereafter, 80 g (1.83 mol) of ethylene oxide was added to the reactor under pressure and allowed to react at 150–160° C. for about 8 hours with stirring, so as to give a liquid phase of polyoxyethylene vitamin E, which was little dispersed in water. It was subjected to addition reaction with 36 g (0.62 mol) of propylene oxide for 8 hours at 145–155° C. in the presence of 0.1 g of methoxy sodium ($CH_3ONa$) to give a yellow liquid phase.

After completion of the reaction, the reactor was purged three times with gaseous nitrogen to remove unreacted ethylene oxide, propylene oxide and 1,4-dioxane, a by-product. The reaction mixture was cooled to about 30°

C., followed by adding a trace amount of citric acid to neutralize the alkaline catalyst. After unreacted vitamin E was removed with toluene, the reaction was purified by column chromatography on Sephadex LH-50 eluting with a chloroform-methanol (1:1, v/v) to afford 328.5 g of polyoxypropylenepolyoxyethylene vitamin E(4) in a liquid phase.

(1) Appearance: a pale yellow liquid phase at room temperature (2) Elemental Analysis: as a relative molecular weight of $C_{38}H_{68}O_6$
Calculated (%): C 73.55; H 10.97; N: 0.00
Found (%): C 72.53; H 11.4; N: 0.03

(3) Yield: 93.9%

Figure 5:
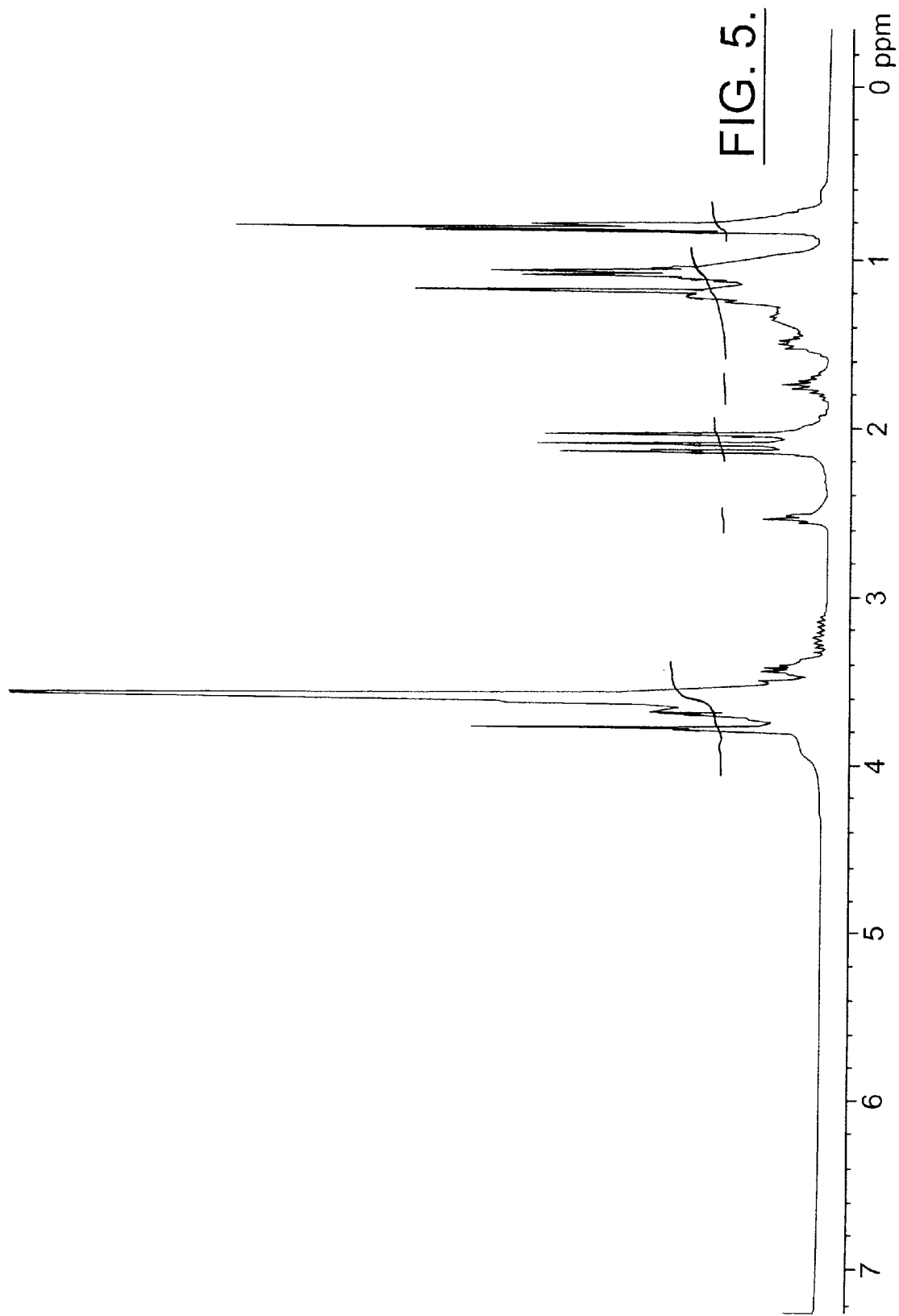
FIG. 5 is an $^1$H-NMR spectrum of the polyoxypropylenepolyoxyethylene vitamin E (4) prepared in Example IV.

(4) Moles of Added Ethylene oxide: 3 moles on average (5) Moles of Added Propylene oxide: 1 moles on average (6) NMR spectrum An $^1$H-NMR spectrum for the polyoxypropylenepolyoxyethylene vitamin E(4) is shown in FIG. 5. In this NMR spectrum, when being compared with the NMR spectrum of FIG. 1, the peak for —OH at 4.1 δ disappears while peaks for the H of polyethylene oxide —$(CH_2CH_2O)_m$— and for the H of the

of polypropylene oxide —$(CH(CH_3)$—$CH_2$—$O)_n$H appear at 3.5–3.8 δ. Also, an H peak of the end —OH of the propylene oxide appears at 3.97 δ and a peak for the of polypropylene oxide $(CH(CH_3)$—$CH_2$—$O)_n$— is additively detected at 1.3 δ.

The spectrum of FIG. 4 is similar in pattern to, but smaller than that of FIG. 2 because the moles of the polyoxyethylene and polyoxypropylene used in this Example were fewer than those of the polyoxyethylene and polyoxypropylene used in Example I.

EXAMPLE V

Preparation of polyoxypropylenepolyoxyethylene vitamin E (5)

In a 2L double stainless steel autoclave were introduced 125 g (0.30 mol) of synthetic vitamin E (dl α-tocopherol) and then, 0.2 g of highly pure KOH (99.9%). The moisture inside the reactor was removed by heating to 77° C. under vacuum of about 740 mmHg for about 30 min.

Thereafter, 600 g (13.64 mol) of ethylene oxide was added to the reactor under pressure and allowed to react at 160–165° C . for about 6 hours with stirring, so as to give a liquid phase of polyoxyethylene vitamin E, which was well dispersed in water. It was subjected to addition reaction with 175 g (1.64 mol) of propylene oxide for 8 hours at 155–160° C. in the presence of 0.15 g of KOH (99.9%) to give a yellow liquid phase.

After completion of the reaction, the reactor was purged three times with gaseous nitrogen to remove unreacted ethylene oxide, propylene oxide and 1,4-dioxane, a by-product. The reaction mixture was cooled to about 40° C., followed by adding a trace amount of citric acid to neutralize the alkaline catalyst. After unreacted vitamin E was removed with toluene, the reaction was purified by column chromatography on Sephadex LH-50 eluting with a chloroform-methanol (1:1, v/v) to afford 893.3 g of polyoxypropylenepolyoxyethylene vitamin E(5) in a liquid phase.

(1) Appearance: a pale yellow solid phase at room temperature (2) Elemental Analysis: as a relative molecular weight of $C_{150}H_{248}O_{58}$
Calculated (%): C 58.5; H 8.1; N: 0.00
Found (%): C 59.2; H 8.0; N: 0.03

(3) Yield: 96.3%

(4) Moles of Added Ethylene oxide: 46 moles on average (5) Moles of Added Propylene oxide: 10 moles on average (6) NMR spectrum An $^1$H-NMR spectrum for the polyoxypropylenepolyoxyethylene vitamin E(5) is shown in FIG. 6. in this NMR spectrum, when being compared with the NMR spectrum of FIG. 1, the peak for —OH at 4.1 δ disappears while peaks for the H of polyethylene oxide —$(CH_2CH_2O)_m$— and for the H of the

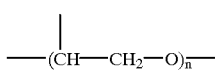

of polypropylene oxide —$(CH(CH_3)$—$CH_2$—$O)_n$H appear at 3.5–3.8 δ. Also, an H peak of the end —OH of the propylene oxide appears at 3.97 δ and a peak for the —$CH_3$ of polypropylene oxide —$(CH(CH_3)$—$CH_2$—$O)_n$— is additively detected at 1.3 δ.

The spectrum of FIG. 4 is similar in pattern to, but taller than that of FIG. 2 because the moles of the polyoxyethylene and polyoxypropylene used in this Example were more than those of the polyoxyethylene and polyoxypropylene used in Example I.

EXAMPLE VI

Preparation of polyoxypropylenepolyoxyethylene vitamin E (6)

The same procedure as in Example III was repeated, except for using 120 g (0.29 mol) of natural vitamin E (α, β, γ and δ-tocopherol mixture) instead of synthetic vitamin E, to afford 485 g of polyoxypropylenepolyoxyethylene vitamin E (21 EO moles and 5 PO moles on average) as a semi-solid phase.

EXAMPLE VII

Anti-Oxidation Activity of Polyoxypropylenepolyoxyethylene Vitamin E

An examination was made of the anti-oxidation activity of the polyoxypropylenepolyoxyethylene vitamin E, using linoleic acid. The linoleic acid used was a reagent purchased from Sigma, U.S.A., comprising linoleic acid 75% and linolenic acid 12.5%.

The polyoxypropylenepolyoxyethylene vitamin E(1) prepared in Example I was added at an amount of 0.5% in the linoleic acid while vitamin E, vitamin E acetate, polyoxyethylene (12EO) vitamin E, polyoxyethylene (20EO) sorbitan monostearate (TWEEN-60), and polyoxyethylene (12EO) nonylphenylether (Igepal-CO880) were also used as references. These samples were stored in an incubator maintained at 40° C. At two days and ten days after the incubation, a peroxide value was determined for each sample. In detail, in a 250 ml Erlenmeyer flask was placed 1.0 g of each of the samples, and 10 ml of chloroform were added to dissolve the sample, after which 15 ml of glacial acetic acid and 1 ml of saturated potassium iodide solution were added and a stopper was put in the flask. After being vigorously shaken, the flask was allowed to stand in a dark place for 5 min. Thereafter, the flask was added with 75 ml of distilled water and vigorously shaken. Free iodine was titrated with a 0.01 N sodium thiosulfate solution, using a starch solution as an indicator. The point at which the solution became colorless was regarded as the end point. The peroxide value was calculated as follows:

$$POV(meq/kg) = \frac{(S-B) \times F}{\text{Amount of Sample (g)}}$$

S: Amount of 0.01 N sodium thiosulfate solution consumed by sample (ml)

B: Amount of 0.01 N sodium thiosulfate solution consumed in blank test tube (ml)

F: Factor of 0.01 N sodium thiosulfate solution

The results are summarized in Table 1, below.

TABLE 1

Peroxide Values

| Samples | After 2 days | After 10 days |
|---|---|---|
| 1. Linoleic Acid (5° C.) | 15.7 | 16.8 |
| 2. Linoleic Acid (40° C.) | 30.6 | 167.2 |
| 3. Linoleic acid + vitamin E (0.5%) | 21.6 | 58.9 |
| 4. Linoleic acid + Acetate of vitamin E | 27.2 | 123.3 |
| 5. Linoleic acid + polyoxypropylenepolyoxyethylene vitamin E(1) (0.5%) | 25.9 | 118.6 |
| 6. Linoleic acid + polyoxypropylenepolyoxyethylene vitamin E(3) (0.5%) | 26.3 | 120.6 |
| 7. Linoleic acid + polyoxypropylenepolyoxyethylene vitamin E(4) (0.5%) | 24.8 | 108.4 |
| 8. Linoleic acid + 12EO vitamin E (0.5%) | 26.0 | 124.6 |
| 9. Linoleic acid + 20EO sorbitan mono stearate (0.5%) | 25.0 | 126.6 |
| 10. Linoleic acid + 12EO nonylphenylether (0.5%) | 28.9 | 178.5 |

As apparent from the data of Table 1, the polyoxypropylenepolyoxyethylene vitamin E (1) prepared in Example I, the polyoxypropylenepolyoxyethylene vitamin E (3) prepared in Example III and the polyoxypropylenepolyoxyethylene vitamin E (4) prepared in Example IV are less potent in anti-oxidation activity than vitamin E, a physiologically active antioxidant, but show similar anti-oxidation activity to that of vitamin E acetate, a stable anti-oxidizing vitamin E derivative, with superiority over polyoxyethylene (12EO), polyoxyethylene (20EO) sorbitan monostearate and polyoxyethylene (12EO) nonylphenylether.

EXAMPLE VIII

Surface Activity of polyoxypropylenepolyoxyethylene vitamin E

In order to make an examination of the surface activity of the novel polyoxypropylenepolyoxyethylene vitamin E, the polyoxypropylenepolyoxyethylene vitamin E prepared in the Example I to VI was tested for surface tension, foaming ability and foam stability, along with polyoxyethylene (24EO) cholesterol and polyoxyethylene (12EO) vitamin E.

1 Foaming Ability and Foam Stability

The foaming ability and foam stability were determined according to a dynamic foam test. First, in a 2 L scaled cylinder with an inner diameter of 10 cm were charged 40 ml of a 0.1% solution of each sample in water and the solution was stirred at 1,000 rpm 20° C. for 1 min with an agimixer. The height of the foam layer thus formed was regarded as foaming ability while the ratio of the volume of the foam layer formed immediately after the stirring to the same maintained at three minutes after the stirring, was denoted as foam stability. The results are given in Table 2, below.

TABLE 2

Foaming Ability and Foam Stability

| Samples | Foaming Ability (cc) | Foam Stability (%) |
|---|---|---|
| 24 EO Cholesterol | 246 | 89.6 |
| 12 EO vitamin E | 125 | 46.5 |
| polyoxypropylenepolyoxyethylene vitamin E(1) | 130 | 43.6 |
| polyoxypropylenepolyoxyethylene vitamin E(3) | 153 | 50.3 |
| polyoxypropylenepolyoxyethylene vitamin E(5) | 251 | 88.2 |

The data of Table 2 demonstrate that the polyoxypropylenepolyoxyethylene vitamin E (5) with 46 moles of ethylene oxide and 10 moles of propylene oxide on average is higher in foaming ability and foam stability than the polyoxypropylenepolyoxyethylene vitamin E (1) and shows almost the same foaming ability and foam stability as the polyoxyethylene (24EO) cholesterol as a reference.

2 Surface Tension

At 20° C., 0.1% solutions of samples in water were measured for surface tension according to the du Nuoy method with the aid of a surface tension balance manufactured by Fisher Scientific. The results are given in Table 3, below.

TABLE 3

Surface Tension in 0.1% Aqueous Solution (20° C.)

| Samples | Surface Tension (dyne/cm) |
|---|---|
| 24 EO cholesterol | 38.4 |
| 12 EO vitamin E | 56.3 |
| polyoxypropylenepolyoxyethylene vitamin E(1) | 49.8 |
| polyoxypropylenepolyoxyethylene vitamin E(2) | 50.5 |
| polyoxypropylenepolyoxyethylene vitamin E(3) | 45.7 |
| polyoxypropylenepolyoxyethylene vitamin E(4) | 61.2 |
| polyoxypropylenepolyoxyethylene vitamin E(5) | 42.5 |

As shown in Table 3, the polyoxypropylenepolyoxyethylene vitamin E (5) has a surface tension of 42.5 dyne/cm, which is slightly higher than that of polyoxyethylene (24EO) cholesterol.

3 Formation of Vesicles

Figure 7A:
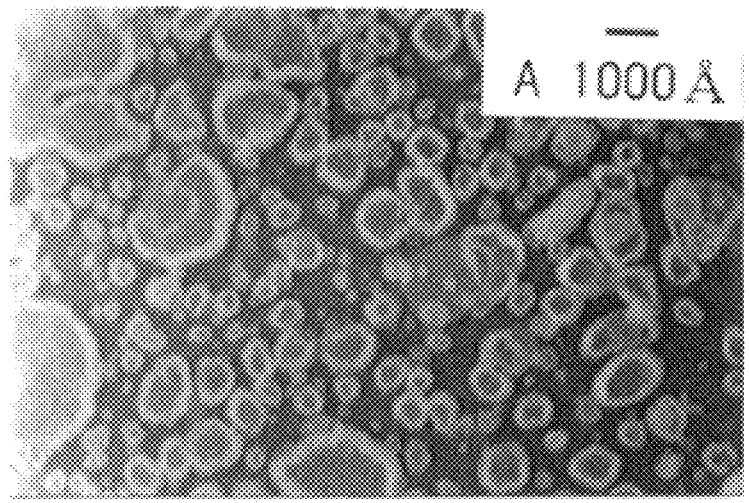
FIG. 7a is an electronic microphotograph showing a vesicle formed by the polyoxypropylenepolyoxyethylene vitamin E (3) prepared in Example III.
Figure 7B:
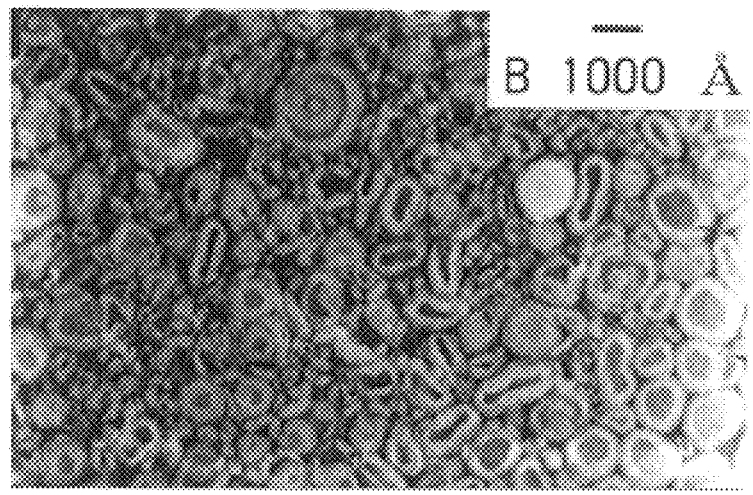
FIG. 7b is an electronic microphotograph showing a vesicle formed by the polyoxypropylenepolyoxyethylene vitamin E (4) prepared in Example IV.

In order to examine another surface action property of the polyoxypropylenepolyoxyethylene vitamin E, vesicles were formed using 0.5% aqueous solutions of the polyoxypropylenepolyoxyethylene vitamin E prepared in Examples III and V. First, the aqueous solutions maintained at 25° C. were stirred with a tip type high frequence generator, added with an equal volume of a 2% uranyl acetate solution and shaken by hand. Subsequently, the resulting solution was dropwise added on a carbon-coated copper grid with a size of 200 mesh and dried at room temperature for about 20 min. Observation was conducted with the aid of an electronic microscope, manufactured by Philips, operating at 80 KV. The electronic microphotographs are shown in FIG. 7. As seen, there were formed close globular vesicles with a bilayer structure.

EXAMPLE IX

Safety in Living Body

1. Eye Irritation Test

In order to evaluate the safety of the novel polyoxypropylenepolyoxyethylene vitamin E, a primary eye irritation test was conducted on rabbits as taught by Draize. The polyoxypropylenepolyoxyethylene vitamin E (5) prepared in Example V, polyoxyethylene (12EO) nonylphenylether and polyoxyethylene (20EO) sorbitan monostearate each was diluted with a 10% aqueous glycerine solution to give a 10% sample solution. This test sample was dropped onto one eye of each of 6 rabbits weighing 2–3 kg while the other eye was used as a control. 24 hours later, the average scores were recorded according to the Draize scoring for ocular lesions. If lesions were present, the time was extended; otherwise, observation was ceased.

The results are given in Table 4, below.

TABLE 4

Eye Irritation Test According to Draize Procedure

| Samples | Avg. Values |
| --- | --- |
| Glycerine (10%) | 0.00 |
| polyoxypropylenepolyoxyethylene vitamin E(1) | 0.12 |
| polyoxypropylenepolyoxyethylene vitamin E(5) | 0.10 |
| 12 EO vitamin E | 0.19 |
| 12 EO nonylphenylether | 0.35 |
| 20 EO sorbitan monostearate | 0.16 |

As seen in Table 4, the polyoxypropylenepolyoxyethylene vitamin E (5) is a weaker irritant than the other test samples, that is, polyoxyethylene (20EO) sorbitan monostearate, polyoxyethylene (12EO) vitamin E and polyoxyethylene (12EO) nonylphenylether and therefore, can be used safely in medicines, foods, and cosmetics, such as elemental cosmetics, make-up cosmetics and hair-care cosmetics. The addition amount of the polyoxypropylenepolyoxyethylene vitamin E according to the present invention is dependent on its purposes and the kinds of the materials it is to be used together with, but preferably on the order of approximately 0.05 to 60% by weight.

2. Patch Test

In order to confirm non-toxicity of the polyoxypropylenepolyoxyethylene vitamin E according to the present invention, a patch test was conducted on the human body according to the Finn Chamber method. The subjects of this test were all females 15–35 years old. A sample material was dropped onto the brachium of each of the subjects and a dermicel tape was bonded thereto. The skin irritations were evaluated as a response rate (%) according to an International Contact Dermatitis Research Group (ICDRG) standard after 24 or 48 hour. The results are given in Table 5, below.

TABLE 5

| | Patch Test | |
| --- | --- | --- |
| | Response Rate (%) | |
| Samples | 24 h | 48 h |
| polyoxypropylenepolyoxyethylene vitamin E(1) | 0.3 | 0.0 |
| polyoxypropylenepolyoxyethylene vitamin E(5) | 0.5 | 0.0 |
| 20 EO sorbitan monostearate | 0.6 | 0.0 |
| 12 EO vitamin E | 1.6 | 0.8 |
| 12 EO nonylphenylether | 2.4 | 2.0 |

The data shown in Table 5 demonstrate the polyoxypropylenepolyoxyethylene vitamin E has no irritations on the skin and is safer to apply to the skin than the controls, polyoxyethylene (20EO) sorbitan monostearate, polyoxyethylene vitamin E and polyoxyethylene (12EO) nonylphenyl ether.

INDUSTRIAL APPLICABILITY

As described hereinbefore, the polyoxypropylenepolyoxyethylene vitamin E of the present invention, which can be prepared by the two-step addition reaction of the anti-oxidant and physiological active vitamin E with ethylene oxide and then with hydrophobic propylene oxide to a proper extent, is of superior anti-oxidation activity with water solubility. The bent chain of the polyoxypropylenepolyoxyethylene vitamin E increases the cross sectional area of the whole molecule, making it difficult for the molecule to penetrate into the skin. Therefore, it is very safe to apply on the skin. In addition, the polyoxypropylenepolyoxyethylene vitamin E has superb surface activity by forming close bilayer vesicle structures, like phospholipids or dialkyl surfactants, so it can be advantageously used in the cosmetic industry, the food industry and the medical industry.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. Polyoxypropylenepolyoxyethylene vitamin E, represented by the following general formula I:

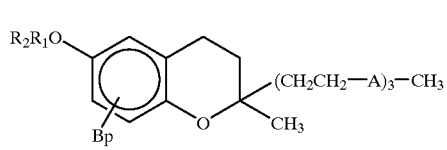

[I]

wherein, $R_1$ is —$(OCH_2CH_2)_m$— wherein m is an integer of 0 to 150;

$R_2$ is

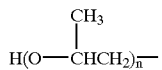

wherein n is an integer of 1 to 200;

A is

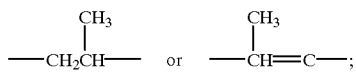

B is —$CH_3$ at the 5-, 7- or 8-position of vitamin E; and p is an integer of 1 or 3.

2. A method for preparing polyoxypropylenepolyoxyethylene vitamin E, represented by the following general formula I:

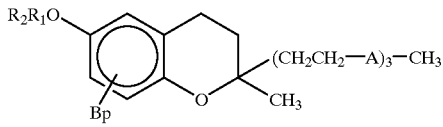

wherein, $R_1$ is —$(OCH_2CH_2)_m$— wherein m is an integer of 0 to 150;

$R_2$ is

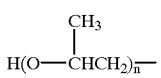

wherein n is an integer of 1 to 200;

A is

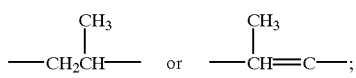

B is —$CH_3$ at the 5-, 7- or 8-position of vitamin E; and p is an integer of 1 or 3, in which the vitamin E represented by the following general formula II:

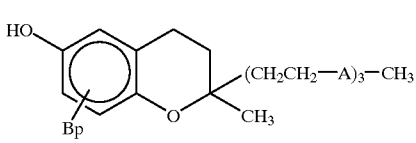

wherein A, B and p each are as defined above, is subjected to addition reaction with ethylene oxide, represented by the following formula III:

in the presence of a catalyst and then, with propylene oxide, represented by the following formula IV;

in the presence of a catalyst.

3. A method as set forth in claim 2, wherein the vitamin E is selected from the group consisting of synthetic vitamin E, natural vitamin E and ester compounds thereof.

4. A method as set forth in claim 3, wherein the synthetic vitamin E is selected from the group consisting of dl-α tocopherol, dl-β tocopherol, dl-γ tocopherol and dl-δ tocopherol.

5. A method as set forth in claim 3, wherein the vitamin E is vitamin E acetate or vitamin E succinate.

6. A method as set forth in claim 2, wherein the polyoxypropylenepolyokyethylene vitamin E has suitable surface activity by selecting m and n from integers ranging from 0 to 150 and from 1 to 200, respectively.

7. A method as set forth in claim 2, wherein the catalyst is an alkaline catalyst selected from $CH_3ONa$, NaOH and KOH or a Lewis acid catalyst selected from $BF_3$, $SnCl_4$ and $SbCl_5$ and is used at an amount of 0.02 to 0.8% by weight in the polyethoxylation step and the polypropoxylation step, each.

8. A method as set forth in claim 2, wherein the addition reaction is carried out at a temperature of 135 to 170° C.

9. A method as set forth in claim 2, wherein the addition reaction is carried out under a pressure of 3.5 to 5.5 kg/cm².

10. A surfactant, comprising the polyoxypropylenepolyoxyethylene vitamin E of claim 1 as an active ingredient.

11. An anti-oxidant, comprising the polyoxypropylenepolyoxyethylene vitamin E of claim 1 as an active ingredient.

12. A humectant, comprising the polyoxypropylenepolyoxyethylene vitamin E of claim 1 as an active ingredient.

* * * * *